United States Patent
Matsuyama et al.

[11] Patent Number: 5,900,941
[45] Date of Patent: May 4, 1999

[54] HIGH SPEED PATTERN INSPECTION METHOD AND SYSTEM

[75] Inventors: Takayoshi Matsuyama; Ken-ichi Kobayashi, both of Kawasaki; Katsuyoshi Nakashima; Yasunori Hada, both of Yokohama, all of Japan

[73] Assignee: Fujitsu Limited, Kawasaki, Japan

[21] Appl. No.: 08/864,964

[22] Filed: May 29, 1997

[30] Foreign Application Priority Data

Jul. 11, 1996 [JP] Japan .................................. 8-295496

[51] Int. Cl.$^6$ .................................................. G01B 11/00
[52] U.S. Cl. ........................ 356/394; 356/376; 356/237
[58] Field of Search .................................. 356/394, 376, 356/237

[56] References Cited

U.S. PATENT DOCUMENTS

| | | | |
|---|---|---|---|
| 4,347,001 | 8/1982 | Levy et al. | 356/398 |
| 4,532,650 | 7/1985 | Wihl et al. | 382/8 |
| 4,555,798 | 11/1985 | Broadbent, Jr. et al. | 382/8 |
| 4,805,123 | 2/1989 | Specht et al. | 364/559 |

FOREIGN PATENT DOCUMENTS 61-245068  10/1986  Japan .

Primary Examiner—Frank G. Font
Assistant Examiner—Reginald A. Ratliff
Attorney, Agent, or Firm—Staas & Halsey

[57] ABSTRACT

A pattern inspection method includes the steps of: copying design data representative of a design pattern in a storage unit; generating index data and storing the index data in the storage unit, the index data indicating data at what position of the design pattern is stored at which location of the storage unit; picking up an image of a real pattern on a stage and generating real pattern data; reading the design data by using the index data in accordance with a position on the real pattern; generating design pattern data in accordance with the read design data; and comparing the real pattern data with the design pattern data to detect any defect in the real pattern data. A pattern inspection method and system is provided which can perform die-to-database inspection at high speed.

30 Claims, 9 Drawing Sheets ns application is based upon Japanese Patent Application No. 8-295496 filed on Nov. 7, 1996, the entire contents of which are incorporated herein by reference.

HIGH SPEED PATTERN INSPECTION METHOD AND SYSTEM

This application is based upon Japanese Patent Application No. 8-295496 filed on Nov. 7, 1996, the entire contents of which are incorporated herein by reference.

BACKGROUND OF THE INVENTION a) Field of the Invention

The present invention relates to pattern inspection for detecting any defect on patterns, specifically fine patterns formed on reticles, masks, or wafers.

In this specification, the term "design data" means both primary and secondary design data. The primary design data is data first prepared for generating a design pattern achieving a design object, and the secondary design data is data generated by editing the primary design data so as to match a specific application, such as exposure data. It is often convenient for defect inspection of real patterns to use exposure pattern data whose storage position is arranged in correspondence with the physical positions of real patterns. For example, data of the MEBES format of ETEC Corp is used. Such data is also called "design data".

b) Description of the Related Art

Patterns of semiconductor integrated circuit devices, liquid crystal display devices, plasma display devices, and other devices are becoming highly dense and integrated. As circuit patterns become complicated, the pattern data amount increases and pattern defects are likely to occur. Since pattern defects may lead to fatal troubles of circuits, pattern defect inspection is essential.

One pattern defect inspection method is to compare a plurality of same real patterns formed. For example, if a plurality of same semiconductor devices are formed on a single semiconductor wafer, there are a plurality of chips having the same pattern. Inspection through comparison between chips is called die-to-die inspection. If a plurality of reticles having the same pattern are produced, patterns of reticles are compared. This inspection is called plate-to-plate inspection.

Inspection through comparison between same patterns can be conducted at relatively high speed by using a plurality of image pick-up optical systems. However, it cannot be judged through die-to-die or plate-to-plate inspection whether a real pattern is coincident with a design pattern. For example, if some of a design pattern are not transferred to a plurality of real patterns, or if an optical system is attached with a foreign particle or the like, and this shape is transferred to a plurality of real patterns at the same position, then these defects cannot be detected and the real patterns are judged as being normal. Dies and plates are not necessary to be discriminated therebetween for the purpose of defect inspection. Therefore, both are collectively called a die hereinafter unless it is specifically used.

One method of judging whether a real pattern is coincident with a design pattern is die-to-database inspection which compares real patterns with design data. Data of such a database generally for a format suitable for the design of patterns, and so an inspection system cannot use it directly. For example, design data for an exposure pattern is made generally more sophisticated and at a higher resolution than design data for other application uses. A plurality of dots on an exposure pattern may be combined to produce one dot for comparison with another pattern. Sometimes the design data can be used for comparison with real patterns only after some proper data processing such as reduction/magnification, rotation, and inversion is executed.

It is therefore necessary to convert the format of design data into a format suitable for die-to-database inspection. All design data of a pattern to be inspected have been conventionally converted at one time collectively to form an inspection database, both in the case of the primary design data and of the secondary design data, such as exposure design data.

Design data is generally formed to have the same size as a real pattern. Reticles are formed at various magnification factors of, for example, 1, 2, 2.5, 4, 5, and 10. A single reticle may sometimes have areas of different magnification factors. Therefore, at each manufacture process, a reticle having a suitable pattern magnification factor has been selected and inspection data matching the pattern magnification factor has been generated.

It takes a very long time to convert design data into inspection data. If design data is missed during the conversion process, the whole conversion process must start again from the beginning. As the integration degree of a pattern rises and the pattern data amount increases, the data conversion time becomes very long. Since an immense amount of design data is processed, it becomes necessary to use a computing system of a large capacity, such as computers and memories. If all the design data and converted inspection data cannot be loaded in a storage unit, it becomes necessary to generate divided portions of inspection data and to perform inspection a plurality of times.

SUMMARY OF THE INVENTION

It is an object of the present invention to provide a pattern inspection method and system capable of high speed die-to-database inspection.

It is another object of the present invention to provide a pattern inspection method and system for die-to-database inspection and other inspections, capable of reducing the capacity of a storage unit and processing a large amount of design data.

According to one aspect of the present invention, there is provided a pattern inspection method comprising the steps of: copying design data representative of a design pattern in a storage unit; generating index data and storing the index data in the storage unit, the index data indicating data at what position of the design pattern is stored at which location of the storage unit; picking up an image of a real pattern on a stage and generating real pattern data; reading the design data by using the index data in accordance with a position on the real pattern; generating design pattern data in accordance with the read design data; and comparing the real pattern data with the design pattern data to detect any defect in the real pattern data.

According to another aspect of the present invention, there is provided a pattern inspection system comprising: a storage unit for storing design data representative of a design pattern and index data indicating data at what position of the design pattern is stored at which location of the storage unit; writing means for writing the design data into the storage unit, generating index data indicating data at what position of the design pattern is stored at which location of the storage unit, and writing the index data into the storage unit; an image pickup optical system for taking an image of a real pattern and generating real pattern data; means for reading the design data by using the index data in accordance with a position on the real pattern; image developing means for generating design pattern data in accordance with the read design data; and defect detecting means for comparing the real pattern data with the design pattern data to detect any defect in the real pattern data.

Since the index data is used, the area of the design pattern corresponding to the presently inspected area of the real pattern can be known. Therefore, only the necessary design data can be read quickly. Since the read design data is small in volume, it can be converted in short time to generate the design pattern data for the real pattern. Since the index data may be generated in parallel with copying the design data, additional time is almost unnecessary. Also the data conversion may be executed in parallel with the stage motion and inspection operation, so that additional time is almost unnecessary.

As above, in accordance with the position of an inspected area on the real pattern, the location of the design pattern is known so that only the necessary design data is read by using the index file.

Since the design data only in the necessary small partition is read, the data conversion is made small in volume. Accordingly, the time required for pattern inspection can be reduced and the logic circuit and memory necessary for the data conversion can be made small in scale.

DETAILED DESCRIPTION OF THE PREFERRED EMBODIMENTS

Figure 1:
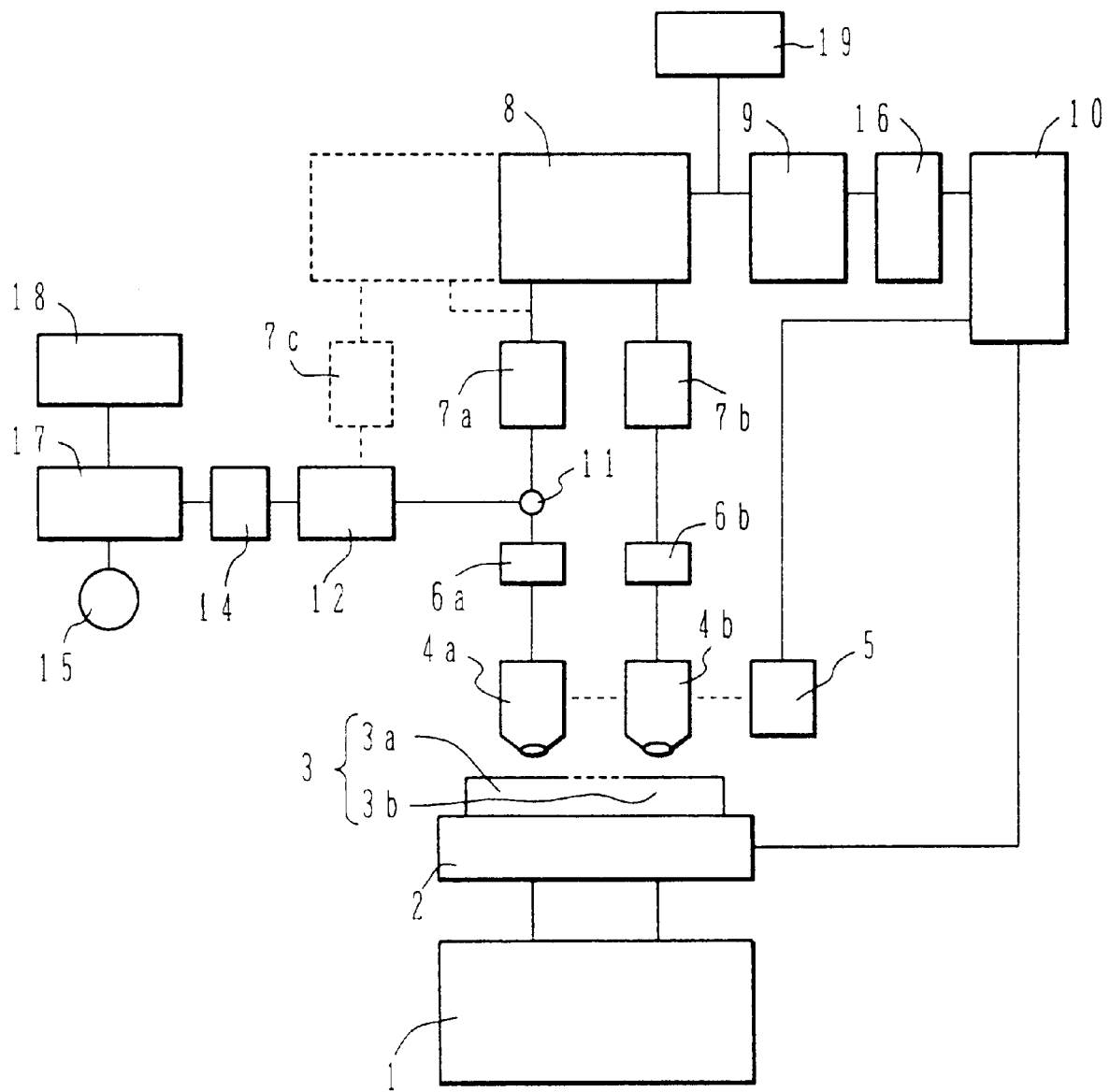
FIG. 1 is a block diagram showing the outline of the structure of a pattern inspection system according to an embodiment of the invention.

FIG. 1 is a block diagram showing the structure of a defect inspection system according to an embodiment of the invention. Illuminating light from a light source 1 is applied to a specimen 3 to be inspected and placed on an XY stage 2. The specimen 3 may be two specimens 3a and 3b. Reference numeral 3 collectively indicates both 3a and 3b. Similarly, reference notation with a numeral followed by an alphabetical letter such as a or b indicates one of a plurality of constituent elements having the same or similar function, and reference notation with only a numeral collectively indicates a plurality of constituent elements or singularly indicates one constituent element. This principle is also applied to reference notation with a character or character string followed by a numeral. The specimens 3a and 3b may be one semiconductor wafer having a plurality of inspection areas, or a pair of reticles having the same pattern.

A pair of objective optical systems 4a and 4b is disposed above the specimens 3a and 3b, and a pair of photosensitive elements 6a and 6b is placed on an image plane of the objective optical systems 4a and 4b. The photosensitive element 6 may be a CCD line sensor. The objective optical system 4 is automatically focussed by an automatic focussing mechanism 5. The specimen 3 can be scanned two-dimensionally by manipulating the XY stage 2. An image in a certain area is picked up by the photosensitive element 6.

Image data picked up with the photosensitive element 6 is stored in a picture memory 7. Although the photosensitive element 6b is always connected to a picture memory 7b, the photosensitive element 6a is selectively connected to a picture memory 7a via a change-over switch 11.

Design data (inclusive of exposure data) 15 is coupled to and copied into a storage unit 17. The storage unit 17 includes a RAM and a hard disk as will be later described. The hard disk may be another type of a memory which can be randomly accessed. An index data producing circuit 18 produces index data when design data is copied from the database 15 into the storage unit 17, and registers the index data in the storage unit 17. The storage unit 17 is connected via a data converter 14 to a picture developer 12. Data in the picture developer 12 is supplied via the change-over switch 11 to the picture memory 7a.

The picture memories 7a and 7b are connected to a pattern synthesis circuit 8. The pattern synthesis circuit 8 can synthesize a plurality of supplied images after position alignment of the images. For example, in accordance with two sets of image data supplied from the picture memories 7a and 7b, two pictures can be superposed and synthesized in the same area and can be indicated in different colors on a display 19. In this case, if two pictures are perfectly coincident, one picture having a color of two mixed colors is synthesized, whereas if two pictures are not coincident, two pictures having different colors are synthesized.

A micro defect detection circuit 9 can detect a micro defect from a plurality of pictures or a synthesized picture thereof. For example, this circuit includes comparators for comparing image data supplied from the picture memories 7a and 7b, detects a defect even if it is very fine, and stores defect information in a defect information memory 16. Detected defects may also be shown on the display 19.

Reading data from the storage unit 17 and the operations of the switch 11, defect detection circuit 9, display 19, and the like are controlled by a system controller 10 which also controls the automatic focussing mechanism 5 and XY stage 2.

An important point of this structure is a provision of an index data producing circuit 18 which generates index data and stores it together with the design data in the storage unit 17 when the design data 15 is copied to the storage unit 17. The index data contains information indicating a location of the storage unit at which data of the design pattern in a particular area is stored. Accordingly, even if data in a particular area is stored dispersively at a plurality of locations of the storage unit 17, the data can be read quickly by referring to the index data.

Under the conditions that the picture developer 12 and the picture memory 7a are connected by the switch 11, as the XY stage 2 is driven and the pattern of the specimen 3 is scanned, the position of the XY stage 2 is detected by the system controller 10. The position of the design pattern corresponding to the image pickup area of the specimen 3 is sent from the system controller 10 to the storage unit 17, and the design data corresponding to the image pickup area is read from the storage unit 17 by referring to the index data.

The data converter 14 converts the coordinate system and representation style of this design data into data having the format matching the real pattern on the specimen 3, and the picture developer 12 forms a design pattern having the same characteristics as the real pattern. This design pattern is supplied to the picture memory 7a so that die-to-database inspection (or plate-to-database inspection) can be performed.

If the switch 11 connects the photosensitive element 6a to the picture memory 7a, die-to-die inspection or plate-to-plate inspection can be performed in a manner similar to conventional methods.

Figure 2A:
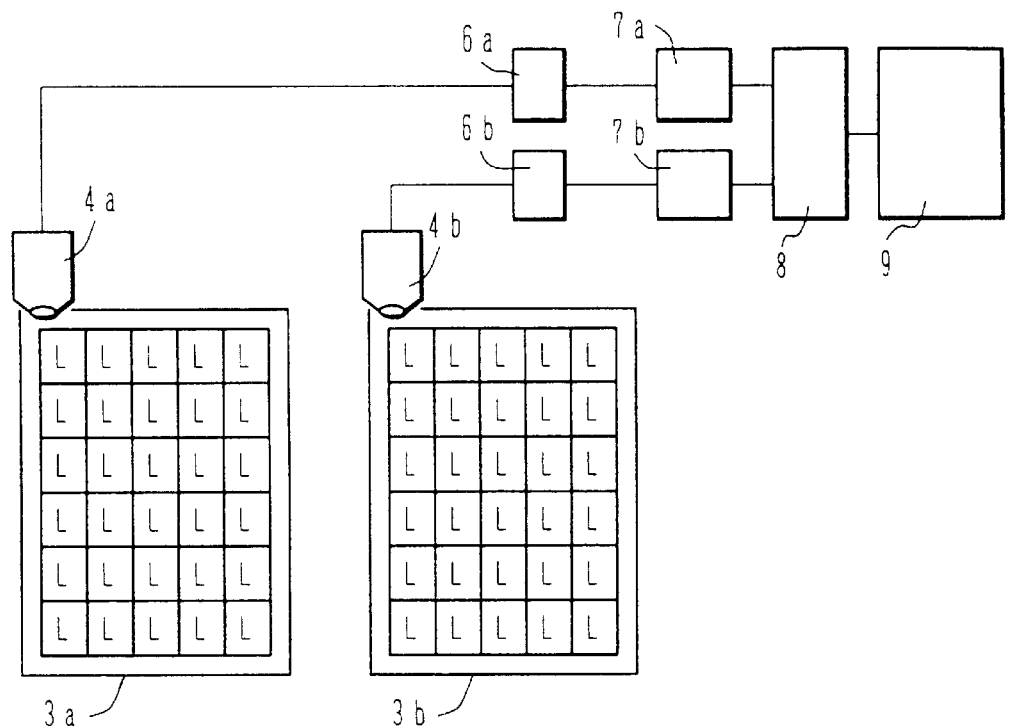
FIGS. 2A and 2B are schematic diagrams illustrating the main circuit portions of the pattern inspection system shown in FIG. 1, respectively used for die-to-die inspection and die-to-database inspection.
Figure 2B:
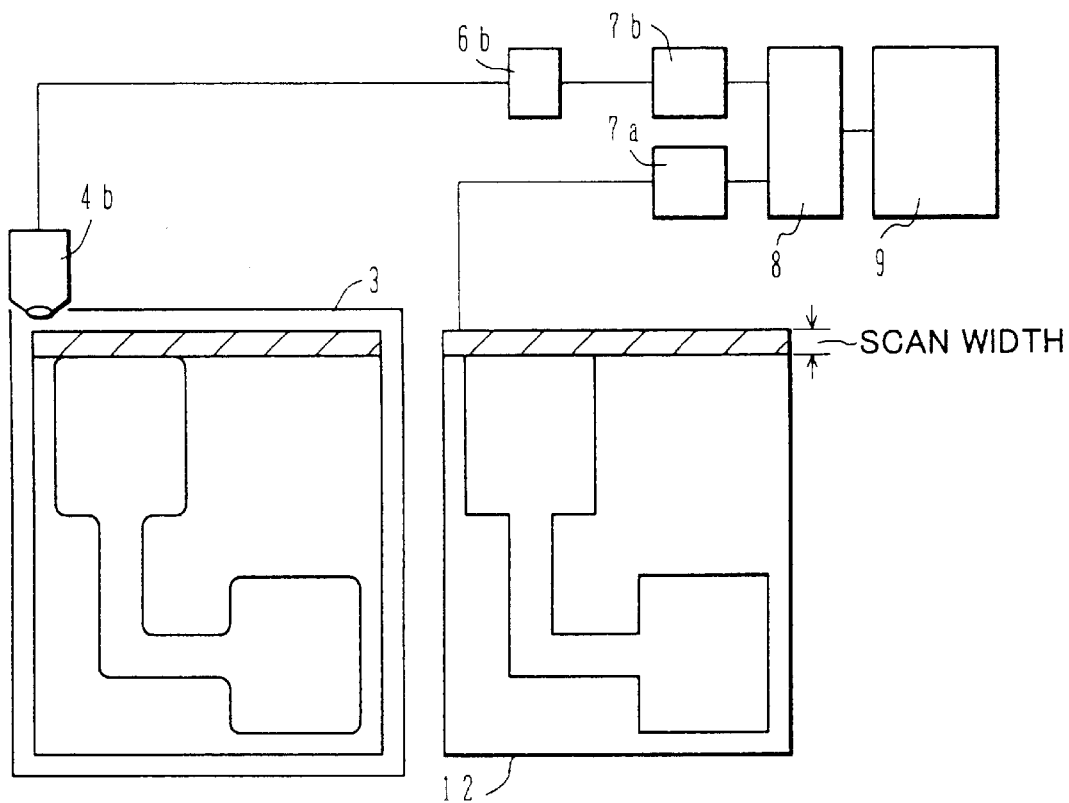

FIGS. 2A and 2B are schematic diagrams illustrating main circuit portions for die-to-die inspection and die-to-database inspection.

Referring to FIG. 2A, two specimens 3a and 3b to be inspected, which specimens are two plates (or two dies) having the same pattern, are disposed under the objective optical systems 4a and 4b in a position alignment state. Images focussed by the objective optical systems 4a and 4b are taken with the photosensitive elements 6a and 6b, and their picture information is stored in the picture memories 7a and 7b. Two sets of picture information are supplied via the pattern synthesis circuit 8 to the defect detection circuit 9 which detects any defect through comparison inspection. The pattern synthesis circuit 8 superposes image data stored in the picture memories 7a and 7b, when necessary, so as to facilitate detection of disagreed picture portions.

Referring to FIG. 2B, a picture of a specimen 3 to be inspected, such as a mask, is focussed by the objective optical system 4b on the photosensitive element 6b and its image data is stored in the picture memory 7b. Of the design pattern developed at the picture developer 12, data corresponding to the picture picked up with the objective optical system 4b is supplied to and stored in the picture memory 7a. Similar to FIG. 2A, data in the picture memories 7a and 7b is supplied via the pattern synthesis circuit 8 to the defect detection circuit 9 to detect a defect.

Although a description has been made for a case where the image developer 12 is connected via the switch 11 to the picture memory 7a, a dedicated picture memory 7c, indicated by a broken line in FIG. 1, may be provided to interconnect the image developer 12 and pattern synthesis circuit 8. In this case, the switch 11 is removed and the photosensitive element 6a is directly connected to the picture memory 7a. The pattern synthesis circuit 8 may be constituted of two partial units, one for the picture memories 7a and 7b and the other for the picture memories 7a and 7c.

With this structure, both die-to-die inspection and die-to-database inspection can be performed concurrently. As compared to separate inspection execution, parallel or concurrent inspection execution can shorten an inspection time. By comparing the results of both inspections, a defect detection sensitivity can be improved. For example, die-to-die inspection detects a defect with high sensitivity even if it is a very fine defect, and die-to-database inspection detects data loss, erroneous pattern generation, position displacement, design rule error, and the like. High speed and high sensitivity inspection can therefore be executed.

For die-to-database inspection, design data read from a database is generally not coincident with a real pattern if the read design data is not processed. A real pattern is often formed by processing the design data through rotation, mirror inversion, reduction, magnification, black/white reversal, or the like. A picture formed at the picture developer 12 shown in FIG. 2B is generated by converting the design data.

FIGS. 3A to 3K are schematic diagrams showing the relationship between a design pattern and real patterns.

Figure 3A:
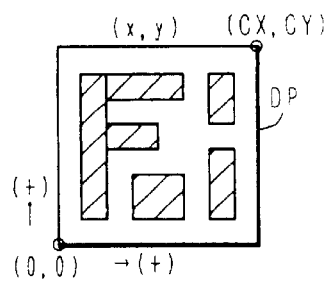
FIGS. 3A to 3K are schematic diagrams showing the relationship between a design pattern and real patterns.

FIG. 3A shows a design pattern DP. Each point of the design pattern DP is represented by a coordinate system whose origin is at the lower left corner, positive direction of an x-axis is in the right direction, and positive direction of a y-axis is in the upward direction. The coordinates at the upper right corner on a diagonal line extending from the origin are represented by (CX, CY). CX and CY correspond to the size of a design pattern. For example, both CX and CY are 100 mm.

Figure 3B:
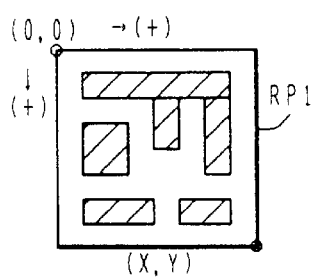
Figure 3C:
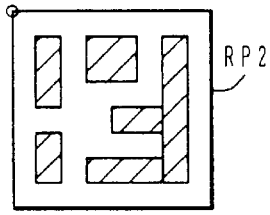
Figure 3D:
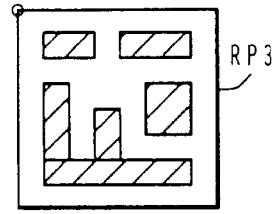

FIGS. 3B to 3K show the shapes of real patterns. For real patterns, the coordinate origin is the upper left corner, the positive direction of the x-axis is in the right direction, and the positive direction of the y-axis is in the downward direction. FIGS. 3B to 3D show real patterns obtained through rotation of the design pattern. FIG. 3B shows a real pattern RP1 obtained through rotation of the design pattern by 90 degrees in the clockwise direction, FIG. 3C shows a real pattern RP2 obtained through rotation of the design pattern by 180 degrees, and FIG. 3D shows a real pattern RP3 obtained through rotation of the design pattern by 270 degrees.

The coordinates of the design pattern DP are represented by (x, y), and those of the real patterns RP1, RP2, and RP3 are represented by (X, Y). The coordinate system (X, Y) of the real pattern RP1 is related with the coordinate system (x, y) of the design pattern by X=y and Y=x. Similarly, the coordinate system of the real pattern RP2 is related by X=CX−x and Y=Y, and that of the real pattern RP3 is related by X=CY−y and Y=CX−x.

Figure 3E:
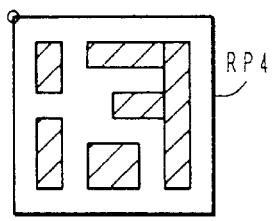

FIG. 3E shows a real pattern RP4 having a mirror inversion relationship with respect to the design pattern DP. Mirror inversion is performed by using the y-axis as a symmetric axis. The coordinate system (X, Y) of the real pattern RP4 is related with by X=CX−x and Y=CY−y.

Figure 3F:
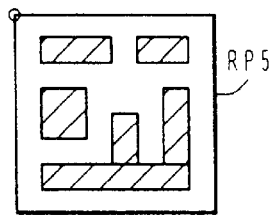
Figure 3G:
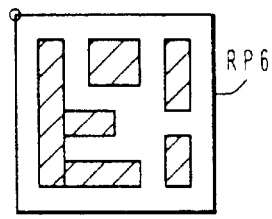
Figure 3H:
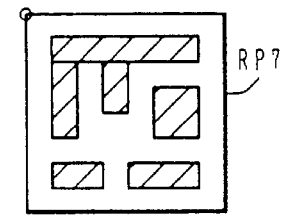

FIGS. 3F, 3G, and 3H show real patterns RP5, RP6, and RP7 obtained through mirror inversion of FIG. 3E and rotation by 90 degrees, 180 degrees, and 270 degrees. The coordinate system of these real patterns is related with that of the design pattern by:

RP5: X=y and Y=CX−y

RP6: X=x and Y=y

RP7: X=CY−y and Y=x.

Figure 3I:
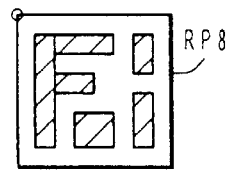
Figure 3J:
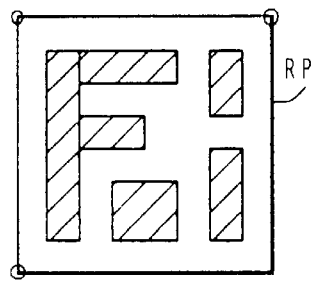

FIGS. 3I and 3J show real patterns RP8 and RP9 obtained through reduction and magnification of the design pattern DP. The coordinate system (X, Y) of the real patterns RP8 and RP9 is related with that of the design pattern by X=X×R and Y=(CY−y)×R where R is a magnification/reduction factor.

Figure 3K:
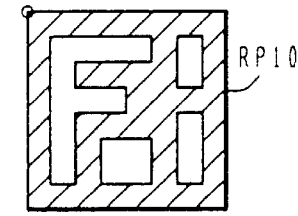

FIG. 3K shows a real pattern RP10 obtained through negative/positive reversal of the design pattern DP. Black and white of a picture are reversed. The relationship between the design pattern and real patterns illustratively described above is not limited thereto. It will be apparent to those skilled in the art that various relationships between a design pattern and real patterns can be obtained through coordinate transformation and negative/positive reversal.

Since the design pattern DP and real pattern RP are expressed by different coordinate systems as described above, the design data is required to be properly converted for use in detecting a defect through a comparison between the real pattern and the design pattern. However, if the amount of design data is enormous and all the design data is to be collectively converted at once, it becomes necessary to use a calculator with a large amount of processing capability and a storage unit with a large capacity.

In this embodiment, the pattern area is divided into small partitions, and a comparison between the design and real patterns is executed in units corresponding to each small partition, to thereby allow a defect inspection system with a small processing capability to compare design and real patterns having a large amount of data.

Figure 4A:
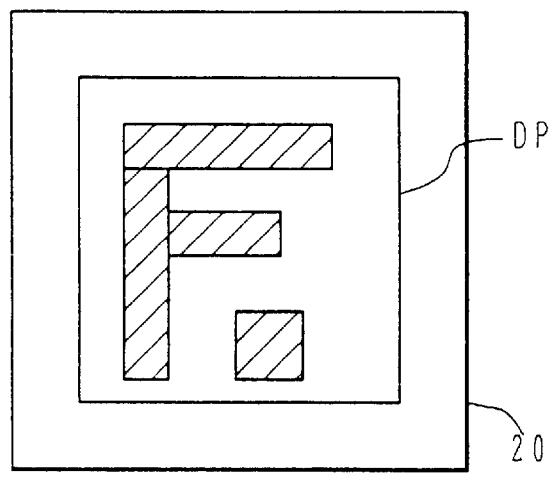
FIGS. 4A to 4C are schematic diagrams illustrating a method of dividing a design pattern into small partitions.
Figure 4B:
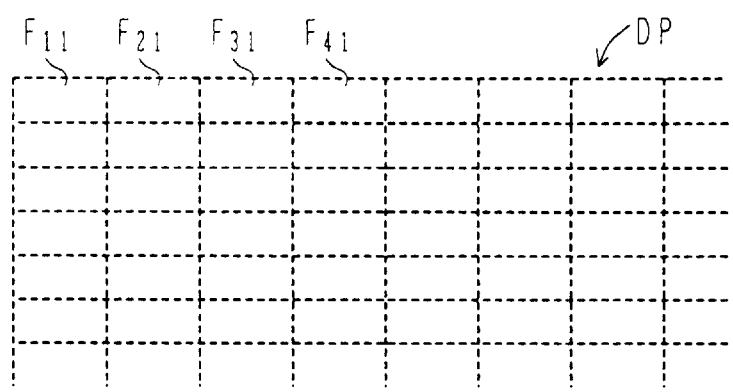
Figure 4C:
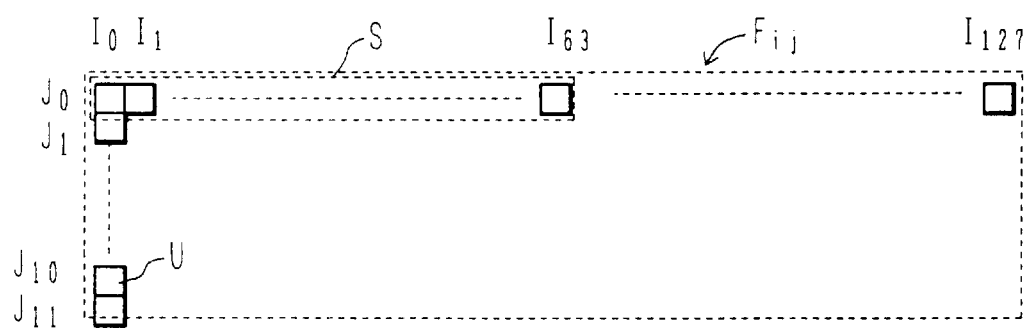

FIGS. 4A to 4C illustrate a method of dividing a design pattern dividing method. FIG. 4A shows an example of a design pattern. The design pattern DP is formed on a reticle 20.

FIG. 4B is an enlarged view of the upper left area of the design pattern DP. Each partition $F_{11}$, $F_{21}$, $F_{31}$, $F_{41}$, . . . (collectively represented by $F_{ij}$) constitutes one view field of the real pattern used for die-to-database inspection. For die-to-database inspection, the picture pattern focussed on the photosensitive element 6b by the objective optical system 4b is inspected in units corresponding to each view field $F_{ij}$.

FIG. 4C is an enlarged view of one view field $F_{ij}$. In a partition of one view field $F_{ij}$, 128 small partitions U in the horizontal direction and 12 small partitions U in the vertical direction are continuously disposed. The vertical size of one view field is a little smaller than the size of 12 small partitions U. This small partition U is called a unit hereinafter. For inspection purpose, an area of 64 units disposed in the horizontal direction is called a segment S. In one view field, 2 segments S are disposed in the horizontal direction and 12 segments S are disposed in the vertical direction. Although specific partitioning is given above by way of example, the partitioning method and the number of units may be set as desired.

For example, the size of one segment is 1638.4 $\mu$m×25.6 $\mu$m. Design data is often processed in unit of pixel. For example, the minimum unit of design data is a 0.05 $\mu$m square, and this minimum unit is given white or black data. A plurality of pixels of design data may be combined to produce one dot corresponding to one pixel of the photosensitive element.

The photosensitive element 6 is not necessary to be able to pick up the image in one view field $F_{ij}$ at a time. For example, a linear sensor having a width of one unit U may be scanned in a zig-zag way to obtain image data of one view field $F_{ij}$.

Design data is stored in the storage unit 17 independently for each unit U. The horizontal array (column) of units U is represented by I0, I1, . . . , I127 and the vertical array (row) is represented by J0, J1, . . . , J11.

Figure 5:
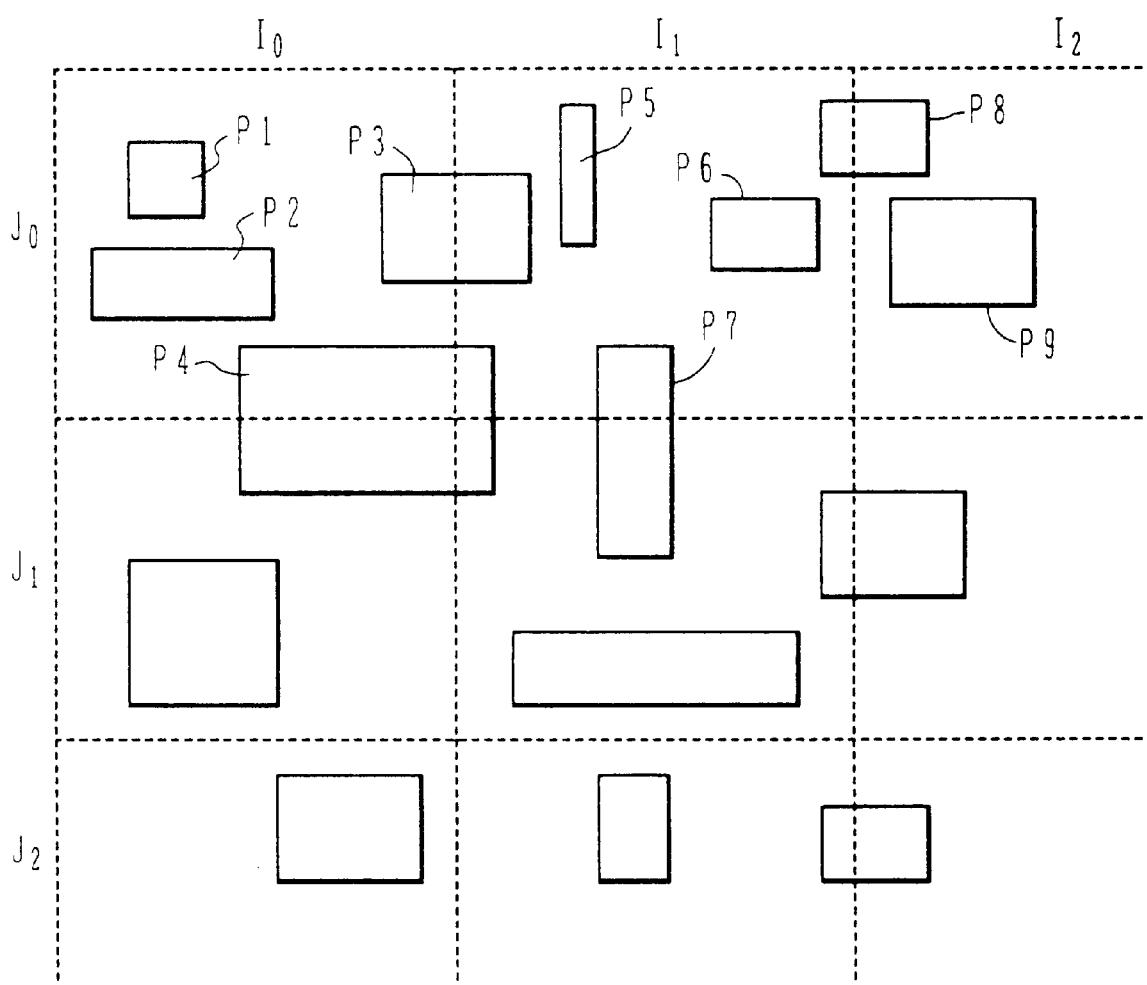
FIG. 5 is a schematic plan view showing the structure of each divided small partition or unit of a design pattern.

FIG. 5 is an enlarged view showing the details of design data. Each unit is identified by (J, I). The unit (J0, I0) contains patterns P1, P2, P3, and P4. Of these patterns, the patterns P3 and P4 extend not only in the unit (J0, I0), but also in other units. The unit (J0, I1) contains patterns P3, P4, P5, P6, P7, and P8.

Each pattern P1, P2, . . . is written as unity in the design data 15, and stored in a unified area of the storage unit 17 when copied thereto. Therefore, data of each pattern can be read if a write start address of the data in the storage unit 17 is known.

However, a pattern $P_{i+1}$ is not necessarily written after a pattern $P_i$. In this embodiment, in order to quickly locate and read design data of a unit (J, I), index data is generated and stored in the storage unit 17.

Figure 6:
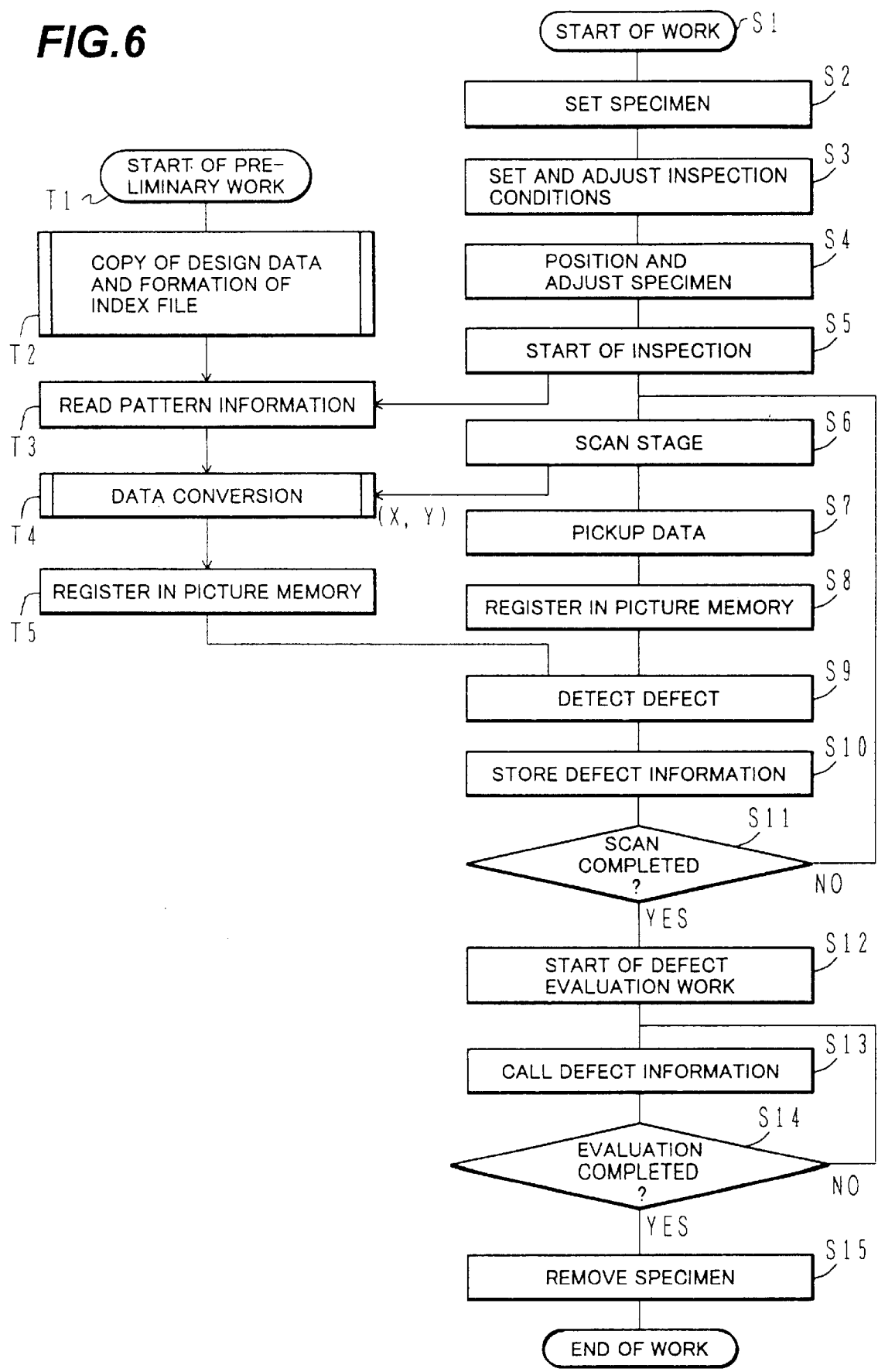
FIG. 6 is a flow chart illustrating the operation of defect inspection.

FIG. 6 is a flow chart illustrating the process of die-to-database inspection. Prior to starting actual inspection, design data converted into a predetermined format is prepared.

After a preliminary work starts at Step T1, copying design data and generating an index file are performed at Step T2. In accordance with a position of a design pattern which can be identified immediately when the design data 15 is copied to the storage unit 17, the index data producing circuit 18 produces index data and stores an index file in the storage unit 17.

Figure 7:
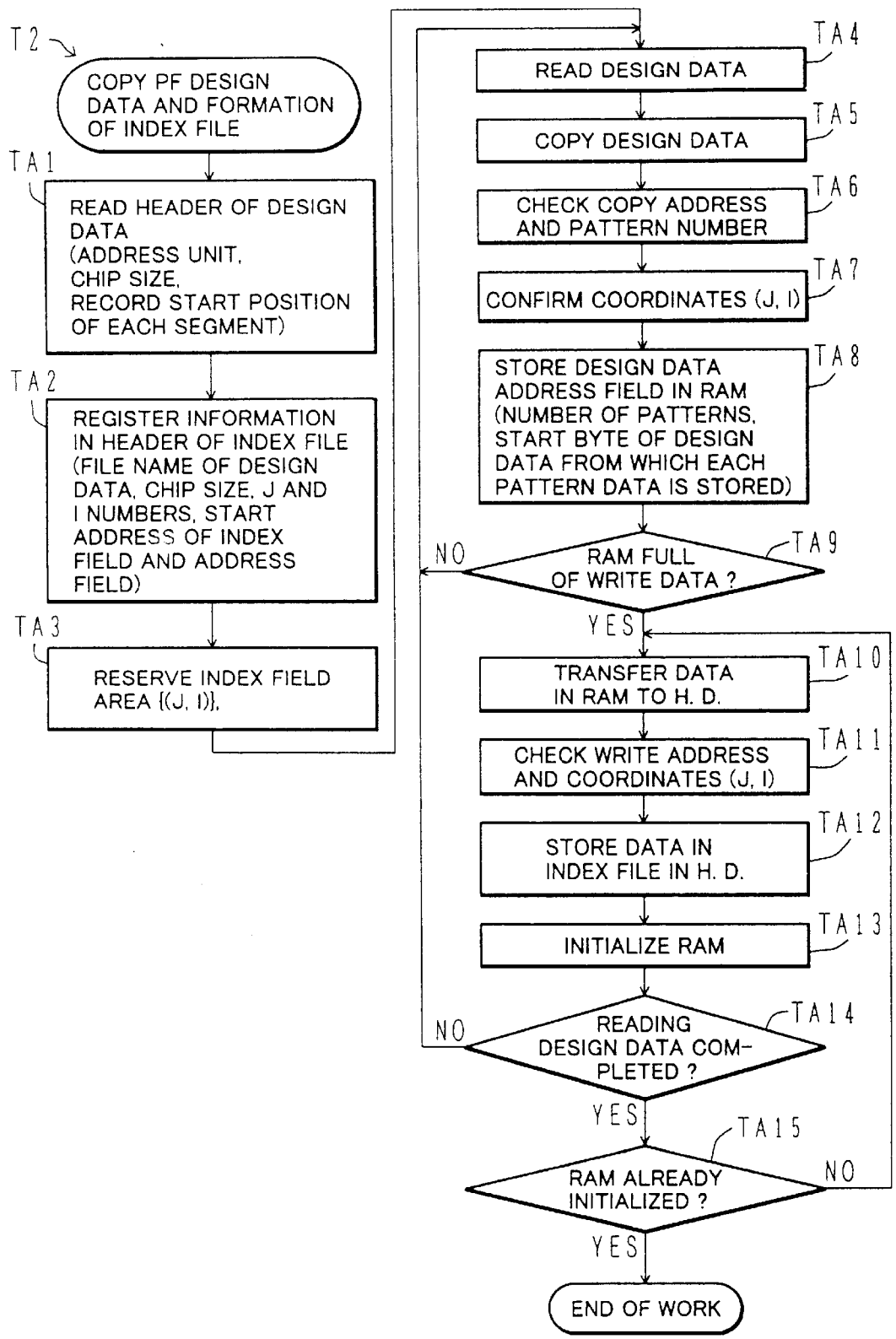
FIG. 7 is a flow chart of a sub-routine illustrating the detailed operations of copying design data and generating an index file during defect inspection.

FIG. 7 is a flow chart of a sub-routine illustrating the operation of copying design data and forming an index file.

As Step T2 of copying design data and forming an index file starts, a header of the design data is read at Step TA1. Generally, the header of the design data contains an address unit, a chip size, a write start position of each segment, and the like. At Step TA2, in accordance with the header of the design data, a header field of the index file is stored with necessary information. The header of the index file contains a file name of design data, a chip size, the J number and I number of the unit array, start addresses of an index field and an address field in the storage area of the index file, and the like.

As described with FIGS. 4A to 4C, the J and I numbers can be known when the size of the design pattern DP is determined. As the J and I numbers are determined, the size of the index field is determined so that the start addresses of the index and address field of the index file stored in the hard disk can be determined. The end address of the address field cannot be determined at this stage.

Figure 8A:
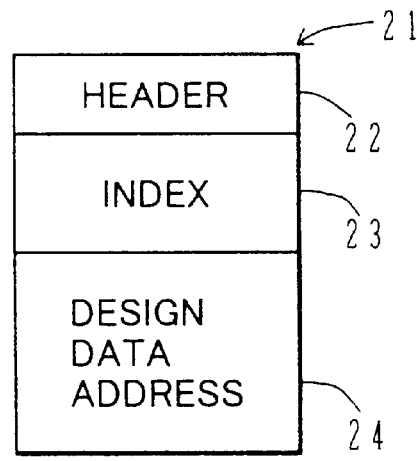
FIGS. 8A to 8C are diagrams showing the structure of the index file.
Figure 8B:
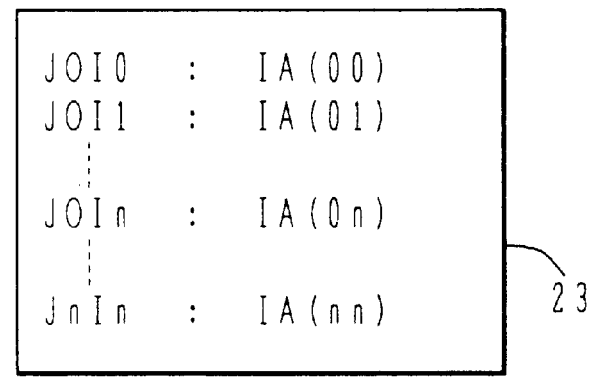
Figure 8C:
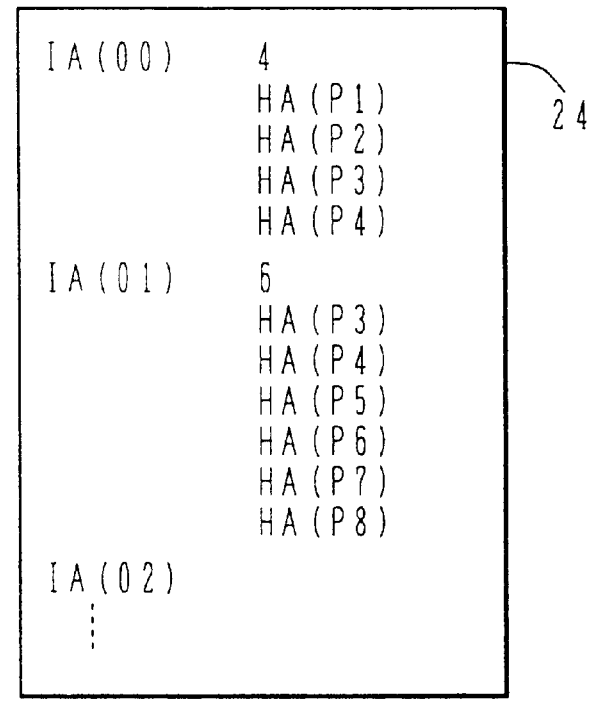

FIGS. 8A to 8C show the structure of the index file. As shown in FIG. 8A, the index file 21 has the header field 22, index field 23, and design data address field 24. As stated above, the file name of the design data, the J and I numbers, the start addresses of the index field 23 and address field 24 in the storage area of the index file, and the like are registered in the header field 22.

FIG. 8B shows the structure of the index field 23. For each unit (J, I) of units (Jn, In), a write start address IA (ji) in the design data address field 24 is registered in the index field 23.

FIG. 8C shows the structure of the design data address field 24. For each unit (J, I), the number of patterns and a write start address HA (Pk) of each pattern P on the hard disk are registered in the design data address field 24.

In the case of the design pattern shown in FIG. 5, write start addresses HA(P1) to HA(P4) on the hard disk are sequentially stored for the patterns P1 to P4 in the unit (J0, I0). The unit (J0, I1) contains the six patterns P3 to P8 and write start addresses HA(P3) to HA(P8) on the hard disk are sequentially registered.

The index file described above is formed so that after the unit of the design pattern is identified, the design data of the unit can be read quickly. While a real pattern is scanned, it is detected whether the scanned area corresponds to which unit of the design pattern, and the index field 23 is referred to. In this manner, it is possible to immediately know at which address on the hard disk the data is stored.

Returning back to FIG. 7, at Step TA3, an area for storing the index field 23 is reserved in the storage unit 17. The size of the index field shown in FIG. 8B can be known when the J and I numbers [(J, I)] are determined, and the area size of the hard disk for storing the index field can be determined. In this manner, Step TA3 reserves the area for storing the index field.

At Step TA4, the design data is read, and at Step TA5 the read design data is copied to the storage unit 17. Along with this copy operation, the copy address of the read design data in the storage unit 17 and the number of patterns are checked at Step TA6 and the coordinates (J, I) of the unit partitioned from the design pattern is confirmed at Step TA7.

As stated earlier, the storage unit 17 includes the hard disk and a RAM. The design data is directly written in the hard disk. At Step TA8, the record address of the design data on the hard disk is stored in RAM. Namely, RAM is set with an area corresponding to the design data address field shown in FIG. 8C. While each pattern is stored in the hard disk, the write start address of each pattern is registered in the design data address field of RAM, while sequentially incrementing the number of patterns during the copy operation. In this manner, RAM stores therein the number of patterns in each unit of the design data stored in the hard disk, and the start byte of the design data from which each pattern data is read.

At Step TA9 it is judged whether RAM is full of write data. If RAM still has memory space, this judgement is NO so that the flow returns to Step TA4 to continue reading design data. If RAM is full of write data, the judgement at Step TA9 is YES so that the flow advances to next Step TA10 in which data in the index file in RAM is stored in the hard disk.

After the design data address of the index file in RAM is transferred to the hard disk, the write start address IA (ji) of the index field 23 is established. This write start address IA (ji) is registered in the index field 23 of RAM.

At Step TA11, the write start address in the index field 23 in RAM and the coordinates (J, I) are checked. At next Step TA12, the data in the index field in RAM is stored in the hard disk. At Step TA13, RAM is initialized after the contents of the index file are transferred to the hard disk.

At next Step TA14, it is checked whether reading of the design data is completed. If not, the flow follows an arrow NO to return to Step TA4. If completed, the flow follows an arrow YES to advance to Step TA15 in which it is judged whether RAM has been initialized. If not initialized, the flow follows an arrow NO to return to Step TA10, whereas if initialized, the flow follows an arrow YES to terminate this routine.

In the above manner, copying the design data and forming an index file are executed at Step T2. By referring to this index file during the real pattern inspection, the design data can be read immediately after the area of the design pattern corresponding to the readout real pattern is located.

Returning back to FIG. 6, for real pattern inspection, as the work starts at Step S1, a specimen is set at Step S2, and inspection conditions are set and adjusted at Step S3. As the inspection conditions, information of a relationship between a design pattern and a real pattern is set, i.e., information of the relationship of the design pattern to a real pattern such as shown in FIGS. 3A to 3K, including rotation, mirror inversion, magnification change, and negative/positive reversal.

Next, at Step S4, a specimen having a real pattern is positioned and adjusted. With positioning and adjustment, a position of the design pattern corresponding to the inspection position of a real pattern can be determined.

After these preliminary operations, inspection starts at Step S5. Real pattern information (rotation, mirror inversion, magnification change, negative/positive reversal, and the like) relative to the design pattern, set as the inspection conditions before the start of inspection, is supplied from the system controller 10 to the data converter 14. This pattern information is registered at Step T3. In accordance with the position of the design pattern, a unit (J, I) of the design pattern is determined.

At Step S6, the stage is scanned to take an image of the pattern in each view field and stored in the picture memory.

While the stage is scanned, the inspection position of the real pattern is known. This scan position (X, Y) of the real pattern is supplied to a read circuit of the storage unit 17.

At Step T4, in accordance with the position of the real pattern and the relationship between the real pattern and the design pattern, the design pattern is read and its data is converted. The data reading step T3 and data conversion step T4 may be carried out in parallel on consecutive units which are consecutively scanned. This data conversion process will be described in detail with reference to FIG. 9.

Figure 9:
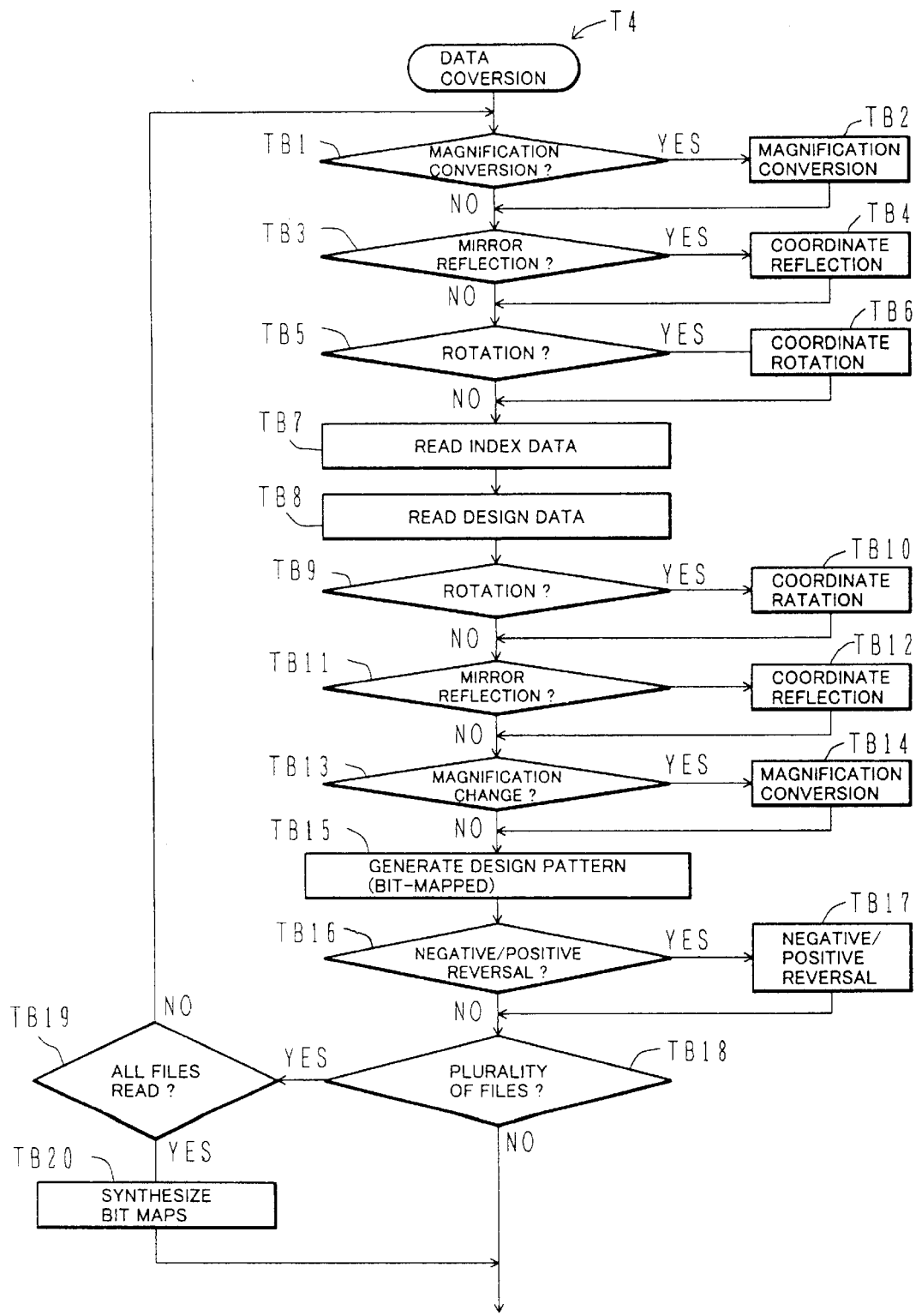
FIG. 9 is a flow chart of a sub-routine illustrating the detailed operations of a data conversion process during defect inspection.

FIG. 9 is a flow chart of a sub-routine illustrating the operation of the data conversion Step T4.

As the data conversion Step T4 starts, at Step TB1 it is judged whether there is a magnification change of the real pattern from the design pattern. If there is a change, the flow follows an arrow YES to execute a magnification conversion at Step TB2 and advances to next Step TB3. If there is no change, the flow follows an arrow NO to bypass Step TB2.

At Step TB3 it is judged whether there is a mirror reflection of the real pattern relative to the design pattern. If there is a mirror reflection, the flow follows an arrow YES to execute a coordinate transformation at Step TB4. If there is no mirror reflection, the flow follows an arrow NO to bypass Step TB4.

At Step TB5 it is judged whether there is a rotation relationship between the real pattern and the design pattern. If there is a rotation, the flow follows an arrow YES to execute a coordinate rotation at Step TB6. If there is no rotation, the flow follows an arrow NO to bypass Step TB6.

In Steps TB1 to TB6, the position in the XY stage coordinate system can be converted into the position in the design data coordinate system. It is therefore possible to know to which position on the design pattern the presently inspecting position on the real pattern corresponds. In the above description, coordinate transformation of magnification change, mirror reflection, and rotation is performed independently. These coordinate transformation operations may be executed collectively by coding a presence/absence of each of such relationships.

At Step TB7, in accordance with the position (i.e., unit position) on the design pattern obtained in the above manner, the index data is read.

At Step TB8, the write position of the design data on the hard disk is identified from the index data, and the design data is read from the identified write position. This design data is stored at the location in the design data coordinate system. Therefore, in order to compare it with the inspected real pattern, the design data coordinate system is required to be transformed into the stage coordinate system.

At Step TB9 it is judged whether the real pattern has a rotation relationship relative to the design pattern. If there is a rotation relationship, the flow follows an arrow YES to rotate the coordinates at Step TB 10. If there is no rotation relationship, the flow follows an arrow NO to bypass Step TB10.

At Step TB11 it is judged whether the real pattern has a mirror reflection relationship relative to the design pattern. If there is a mirror reflection relationship, the flow follows an arrow YES to execute the coordinate reflection at Step TB 12. If there is no mirror reflection relationship, the flow follows an arrow NO to bypass Step TB12. At Step TB13 it is judged whether the real pattern has a magnification change relationship relative to the design pattern. If there is a magnification change relationship, the flow follows an arrow YES to execute the magnification conversion at Step TB 14. If there is no magnification change relationship, the flow follows an arrow NO to bypass Step TB14.

I Steps TB9 to TB14, the coordinates of the read design pattern are converted into the coordinates of the real pattern. Similar to Steps TB1 to TB6, the coordinate transformation operations at Steps TB10, TB12, and TB14 may be executed collectively at a time.

At Step TB15, the coordinate transformed design pattern is developed and bit-mapped.

If the photosensitive element 6b is made of a CCD image pickup element or the like, image data of a detected real pattern is bit-map data. Since the design data developed at Step TB15 is bit-mapped matching the real pattern, it becomes possible to compare each bit pair and detect a defect.

A precision of a design pattern is generally higher than the photosensitive element 6. If the design data is directly bit-mapped, bits of the design pattern cannot be compared with bits of the real pattern in many cases. In such cases, a set of a plurality of bits of the design pattern is collectively bit-mapped so that each pair of bits of the design and real patterns can be compared. For example, 2×2 pixels or 3×3 pixels of the design pattern are converted into one bit.

At Step TB16 it is judged whether the real pattern has a negative/positive relationship relative to the design pattern. If there is a negative/positive relationship, the flow follows an arrow YES to execute a negative/positive reversal of the bit-mapped design pattern at Step TB17. Instead of the design pattern, the real pattern may be subjected to a negative/positive reversal. If there is no negative/positive reversal, the flow follows an arrow NO to bypass Step TB17.

At Step TB18 it is judged whether the design data has a plurality of files. If it has a plurality of files, the flow follows an arrow YES to advance to Step TB19 whereat it is judged whether reading all files has been completed. If not completed, the flow follows an arrow NO to return to Step TB1 to form a new bit map of the next file.

If reading all files has been completed, the flow follows an arrow YES to synthesize bit maps of all files at Step TB20. A transparent area has a priority over other areas in synthesizing. Namely, a transparent area in any one of bits maps becomes also a transparent area in the synthesized bit map. Although a bit map is formed for each file in the above description, a bit map of each file may be overwritten in one bit map.

If there is no plurality of files at Step TB18 or if there is a plurality of files and Step TB20 is completed, then the data conversion Step T4 is terminated.

Returning back to FIG. 6, after the read design data has been converted at Step T4, the design pattern converted into the stage coordinate system is registered in the picture memory 7a at Step T5.

As the stage scan is executed at Step S6, a real pattern is picked up by the objective optical system 4b and photosensitive element 6b at Step S7. In accordance with the picture data of the picked-up real pattern, the data of the real pattern is registered in the picture memory 7b at Step S8.

At Step S9, a defect is detected by using the pattern data registered in the picture memories 7a and 7b.

At Step S10, detected defect information is registered in the defect information memory 16.

At Step S11 it is checked whether scanning of the real pattern has been completed. If not, the flow follows an arrow NO to return to Step S6. If completed, the flow follows an arrow YES to advance to Step S12.

At Step S12 an evaluation work for a detected defect starts. At Step S13 the registered defect information is read to evaluate it. Although the real pattern reflects the design pattern, it is affected by interference, or the like, while the real pattern passes through optical systems, electron lens systems, or the like. Therefore, there are some disagreed areas between the real and design patterns which do not affect a circuit operation at all. In such a case, disagreed patterns are not judged as a defect.

At Step S14 it is checked whether the defect evaluation work has been completed. If not, the flow follows an arrow NO to return to Step S13, whereas if completed, the flow follows an arrow YES to advance to Step S15 in which the inspected specimen is dismounted. The defect inspection is completed in the above-described manner.

The present invention has been described in connection with the preferred embodiments. The invention is not limited only to the above embodiments. For example, in the above embodiment, although two sets of the objective optical system, photosensitive element, and picture memory are used, three or more sets of these may be used. The structure of the index file is not limited only to the above so long as the index file can locate the storage area of the design data of each small partition. It is apparent that various modifications, improvements, combinations, and the like can be made by those skilled in the art.

We claim:

1. A pattern inspection method comprising the steps of:
    copying design data representative of a design pattern in a storage unit;
    generating index data and storing the generated index data in the storage unit, the index data indicating where data corresponding to an area of the design pattern is stored in the storage unit;
    imaging a real pattern on a stage and generating real pattern data;
    reading the design data using the generated index data corresponding to a position of the real pattern;
    generating design pattern data corresponding to the read design data; and
    comparing the real pattern data with the design pattern data to detect defects in the real pattern data.

2. A pattern inspection method according to claim 1, wherein said imaging step is executed in units corresponding to a small partition of the real pattern, and said reading step reads the design data corresponding to the small partition.

3. A pattern inspection method according to claim 2, wherein the design pattern and the real pattern have different coordinate systems, and said reading step and said design pattern data generating step execute data conversion, including converting the coordinate systems.

4. A pattern inspection method according to claim 3, wherein the different coordinate systems are related with at least one of relationships including rotation, mirror reflection, and magnification/reduction.

5. A pattern inspection method according to claim 1, wherein said reading step includes the steps of:
    converting coordinates of a small partition of the real pattern into coordinates of the design pattern;
    searching the index data corresponding to the coordinates of the design pattern to obtain an address in the storage unit; and
    reading design data of the design pattern, corresponding to the small partition, from the obtained address of the storage unit.

6. A pattern inspection method according to claim 5, wherein said design pattern data generating step includes the steps of:

converting coordinates of the read design data from a design pattern coordinate system into a real pattern coordinate system; and generating the design pattern data in accordance with the converted coordinates of the design data.

7. A pattern inspection method according to claim 2, wherein said imaging step includes the step of consecutively scanning the real pattern, and said reading step and said design pattern data generating step execute processes in parallel on a plurality of consecutive small partitions of the real pattern.

8. A pattern inspection method according to claim 1, wherein the design data is stored in a plurality of files, and said copying step, said index data generating step, and said reading step are performed for each file.

9. A pattern inspection method according to claim 8, wherein said design pattern data generating step accumulates a transparent area in each file to generate the design pattern data.

10. A pattern inspection method according to claim 1, wherein the design pattern and the real pattern have a relationship of a negative/positive reversal, and said design pattern data generating step includes the step of executing a negative/positive reversal of the design data.

11. A pattern inspection method according to claim 1, wherein said index data generating step is executed in parallel with said copying step.

12. A pattern inspection method according to claim 1, wherein said index data generating step divides the design data into data of small partitions, and the generated index data indicates an address where information corresponding to data of each small partition is stored in the storage unit.

13. A pattern inspection method according to claim 12, wherein said index data generating step includes the step of forming a table containing the number of patterns located in each small partition and a design data write start address indicating an address where information corresponding to each of the number of patterns is stored in said storage unit.

14. A pattern inspection method according to claim 13, wherein the index data includes a header part indicating a size of the design pattern, an index part indicating, for each of the small partitions of the design pattern, an address of the design data in each small partition, and a design data address part indicating, for each small partition, the number of patterns and a write start address of each pattern.

15. A pattern inspection method according to claim 13, wherein if one pattern is disposed in a plurality of small partitions, the write start address in the index data is the same for all the plurality of small partitions.

16. A pattern inspection system comprising:

a storage unit for storing design data corresponding to a design pattern having a plurality of data positions, and for storing index data indicating a location where data corresponding to each of the plurality of data positions of the design pattern is stored in the storage unit;

writing means for writing the design data into the storage unit, generating the index data, and writing the index data into the storage unit;

an image pickup optical system for imaging a real pattern and generating real pattern data;

means for reading the design data using the index data corresponding to a position of the real pattern;

image developing means for generating design pattern data in accordance with the read design data; and defect detecting means for comparing the real pattern data with the design pattern data to detect defects in the real pattern data.

17. A pattern inspection system according to claim 16, wherein the design pattern is divided into small partitions, and wherein the index data includes a header part indicating a size of the design pattern, an index part indicating, for each partition, an address where the design data in each small partition is stored in the storage unit, and a design data address part indicating, for each small partition, a number of patterns and a write start address of each pattern in the storage unit.

18. A pattern inspection method according to claim 17, wherein if one pattern is disposed in a plurality of small partitions, the write start address in the index data is the same for all the plurality of small partitions.

19. A pattern inspection method comprising the steps of:

generating index data indicating where design data corresponding to an area of a design pattern is located;

reading design data from the generated index data corresponding to a real pattern;

converting coordinates of the read design data to coordinates of the real pattern;

generating design pattern data corresponding to the converted read design data; and comparing the real pattern data with the design pattern data to detect defects in the real pattern data.

20. The pattern inspection method of claim 19, said reading step further comprising imaging a real pattern in units corresponding to a partition of the real pattern and reading design data from the generated index data corresponding to the units.

21. A pattern inspection method according to claim 19, said reading step further comprising:

converting coordinates of a small partition of the real pattern into coordinates of the design pattern;

searching the index data corresponding to the coordinates of the design pattern to obtain an address; and reading design data of the design pattern, corresponding to the small partition, from the obtained address.

22. A pattern inspection method according to claim 20, wherein said imaging includes consecutively scanning the real pattern, and said design data reading step and said design pattern data generating step execute processes in parallel on a plurality of consecutive small partitions of the real pattern.

23. A pattern inspection method according to claim 19, further comprising the step of copying design data of a design pattern, wherein the design data is stored in a plurality of files, and said copying step, said index data generating step, and said design data reading step are performed for each of the plurality of files.

24. A pattern inspection method according to claim 19, wherein said design pattern data generating step accumulates a transparent area in each of the plurality of files to generate the design pattern data.

25. A pattern inspection method according to claim 19, wherein the design pattern and the real pattern have a relationship of a negative/positive reversal, and said design pattern data generating step includes executing a negative/positive reversal of the design data.

26. A pattern inspection method according to claim 19, wherein said index data generating step divides the design data into partitions, and the generated index data indicates an address where information corresponding to the partitions is stored.

27. A pattern inspection method according to claim 26, wherein said index data generating step includes forming a table containing the number of patterns located in each of the partitions and a design data write start address indicates an address where information corresponding to each of the number of patterns is stored.

28. A pattern inspection method according to claim 27, wherein the index data includes a header part indicating a size of the design pattern, an index part indicating, for each of the partitions, an address of the design data in each of the partitions, and a design data address part indicating, for each of the partitions, the number of patterns and a write start address of each pattern.

29. A pattern inspection method according to claim 27, wherein if a pattern of the number of patterns is disposed in more than one of the partitions, the write address in the generated index data is the same for all of the more than one partitions.

30. A pattern inspection system for detecting defects on a real pattern, comprising:
- a storage device to store design data of a design pattern and index data indicating a location of data corresponding to data positions of the design pattern in the storage device;
- a reading device to read the stored design data that corresponds to the real pattern, and to convert coordinates of the read design data into coordinates of the real pattern;
- an imaging device to generate design pattern data corresponding to the read design data; and
- a detecting device to compare the real pattern data with the design pattern data.

* * * * *

UNITED STATES PATENT AND TRADEMARK OFFICE
CERTIFICATE OF CORRECTION

PATENT NO. : 5,900,941
DATED : May 4, 1999
INVENTOR(S) : Takayoshi Matsuyama, et. al.

It is certified that error appears in the above-identified patent and that said Letters Patent is hereby corrected as shown below:

On the title page, [73] Assignee, please add --LASERTEC CORPORATION, YOKOHAMA, JAPAN--.

Signed and Sealed this

Twenty-first Day of September, 1999

Attest:

Q. TODD DICKINSON

*Attesting Officer*  *Acting Commissioner of Patents and Trademarks*